(12) United States Patent
Takahashi

(10) Patent No.: US 7,717,002 B2
(45) Date of Patent: May 18, 2010

(54) EXHAUST GAS DILUTION DEVICE

(75) Inventor: Yasushi Takahashi, Amagasaki (JP)

(73) Assignee: Horiba, Ltd., Kyoto (JP)

( * ) Notice: Subject to any disclaimer, the term of this patent is extended or adjusted under 35 U.S.C. 154(b) by 219 days.

(21) Appl. No.: 11/915,525

(22) PCT Filed: May 23, 2006

(86) PCT No.: PCT/JP2006/310221

§ 371 (c)(1),
(2), (4) Date: Nov. 26, 2007

(87) PCT Pub. No.: WO2006/132081

PCT Pub. Date: Dec. 14, 2006

(65) Prior Publication Data

US 2009/0084200 A1    Apr. 2, 2009

(30) Foreign Application Priority Data

Jun. 9, 2005    (JP) .............................. 2005-169085

(51) Int. Cl.
*G01N 1/10* (2006.01)
(52) U.S. Cl. ................................. 73/864.73
(58) Field of Classification Search .............. 73/864.73, 73/864.33
See application file for complete search history.

(56) References Cited

U.S. PATENT DOCUMENTS 3,933,618 A * 1/1976 Patton ............................ 48/77

FOREIGN PATENT DOCUMENTS

| JP | 56132545 | 10/1981 |
|----|----------|---------|
| JP | 586903 | 2/1983 |
| JP | 6249766 | 9/1994 |
| JP | 6265453 | 9/1994 |
| JP | 2000329661 | 11/2000 |
| JP | 2002333389 | 11/2002 |
| JP | 3502060 | 12/2003 |
| JP | 3634037 | 1/2005 |
| JP | 3670924 | 4/2005 |

* cited by examiner

*Primary Examiner*—Hezron Williams
*Assistant Examiner*—Alex Devito
(74) *Attorney, Agent, or Firm*—Brooks Kushman P.C.

(57) ABSTRACT

An exhaust gas dilution device 1 is to prevent a temperature of dilution gas from being raised under the influence of the temperature of the exhaust gas before the dilution gas is mixed with the exhaust gas. The exhaust gas dilution device 1 comprises an exhaust gas circulation pipe 101 to circulate the exhaust gas G, a mixing section 102 that is arranged in the exhaust gas circulation pipe 101 and that has an orifice 17, and a dilution gas supply pipe 14 that opens at the mixing section 102 and that supplies dilution gas W to the exhaust gas circulation pipe 101. The dilution gas supply pipe 14 is arranged spaced apart from the exhaust gas circulation pipe 101 until it reaches the mixing section 102.

10 Claims, 12 Drawing Sheets

EXHAUST GAS DILUTION DEVICE

FIELD OF THE ART

This invention relates to an exhaust gas dilution device that dilutes exhaust gas in order to analyze material components contained in the exhaust gas of automobiles.

BACKGROUND ART

In case of catching and quantitative-analyzing PM (Particulate matters such as soot or the like) contained in exhaust gas of, for example, a diesel engine by the use of a filter, an exhaust gas dilution device that dilutes the exhaust gas by adding air for dilution is used.

Conventionally, this kind of the exhaust gas dilution device extracts (samples) exhaust gas of an automobile and circulates the extracted exhaust gas to an analyzer through an exhaust gas circulation pipe as shown in, for example, the patent document 1 and the patent document 2. Then the exhaust gas is diluted by mixing the dilution gas to be supplied to the dilution gas supply pipe at a predetermined ratio in a mixing section arranged on the exhaust gas circulation pipe.

The dilution gas supply pipe makes a contact with the exhaust gas circulation pipe until the dilution gas is supplied to the mixing section or the dilution gas supplied from the dilution gas supply pipe passes a surrounding area of the exhaust gas circulation pipe.

With this arrangement, however, a temperature of the dilution gas rises because the dilution gas is affected from the temperature of the exhaust gas through the exhaust gas circulation pipe, or through the exhaust gas circulation pipe and the dilution gas supply pipe, then the exhaust gas can not be mixed with the dilution gas at a predetermined temperature, thereby having an effect on the analysis result.
Patent document 1: Japan patent laid-open No. 2002-333389
Patent document 2: Japan patent laid-open No. 2000-329661

DISCLOSURE OF THE INVENTION

Problems to be Solved by the Invention

Then the present claimed invention intends to solve all of the problems and an object of this invention is to prevent a temperature of the dilution gas from rising due to the temperature of the exhaust gas supply pipe prior to mixing the exhaust gas with the dilution gas.

Means to Solve the Problems

More specifically, the exhaust gas dilution device in accordance with this invention is an exhaust gas dilution device that dilutes exhaust gas for analyzing a substance contained in the exhaust gas, and comprises an exhaust gas circulation pipe that circulates the exhaust gas, a mixing section that is arranged in a midstream of the exhaust gas circulation pipe and that has an orifice, and a dilution gas supply pipe that has an opening at the mixing section and that supplies dilution gas to the exhaust gas circulation pipe, and is characterized by that the dilution gas supply pipe is arranged spaced apart from the exhaust gas circulation pipe until it reaches the opening.

In accordance with this arrangement, since the dilution gas supply pipe and the exhaust gas circulation pipe are arranged spaced apart spatially, a temperature of the dilution gas can be prevented from rising prior to mixing the exhaust gas and the dilution gas due to an increased temperature of the exhaust gas circulation pipe. As a result, it is possible to preferably control the temperature of the exhaust gas after dilution.

In addition, in order to dilute the exhaust gas uniformly, it is preferable that two or more dilution gas supply pipes are provided.

Furthermore, in order to dilute the exhaust gas furthermore uniformly, it is preferable that the openings at the mixing section of the dilution gas supply pipe are arranged at a surrounding area of the exhaust gas circulation pipe at even intervals.

In order to improve precision of measurement further more with equalizing the condition of each dilution gas that circulates in each of the dilution gas circulation pipes, it is preferable that each of the dilution gas supply pipes has the same length.

In order to make it possible to dilute the exhaust gas more uniformly by making use of generation of air turbulence due to the orifice, it is preferable that the exhaust gas circulation pipe comprises the exhaust gas supply pipe to supply the exhaust gas prior to dilution and an exhaust gas transport pipe to circulate the exhaust gas after dilution, and an exhaust gas supply opening to supply the exhaust gas to the mixing section is arranged on the downstream side of the orifice.

In order to make it easy to mix the dilution gas with the exhaust gas by leading the dilution gas toward the opening of the exhaust gas supply pipe, it is preferable to comprise a guide face to guide the dilution gas to be supplied from the dilution gas supply pipe toward a direction (an opening of the exhaust gas supply pipe) toward which the exhaust gas flows.

Furthermore, in order to preferably prevent the temperature of the dilution gas from changing, it is preferable that a heat dissipation mechanism is arranged at a surrounding area of the mixing section.

Effect of the Invention

In accordance with the invention having the above-mentioned arrangement, since the dilution gas supply pipe and the exhaust gas circulation pipe are arranged spaced apart spatially, a temperature of the dilution gas can be prevented from rising due to an increased temperature of the exhaust gas circulation pipe prior to mixing the exhaust gas with the dilution gas. As a result, it is possible to preferably control the temperature of the exhaust gas after dilution, thereby improving an accuracy of the analysis results.

EXPLANATION OF THE REFERENCE NUMERAL

1 . . . exhaust gas dilution device, G . . . exhaust gas, 101 . . . exhaust gas circulation pipe, 17 . . . orifice, 102 . . . mixing section, W . . . dilution gas, 14 . . . dilution gas supply pipe, 132C . . . guide face, 11 . . . exhaust gas supply pipe, 112 . . . exhaust gas supply opening, 15 . . . heat dissipation mechanism (heat dissipation bore)

BEST MODES OF EMBODYING THE INVENTION

Figure 1:
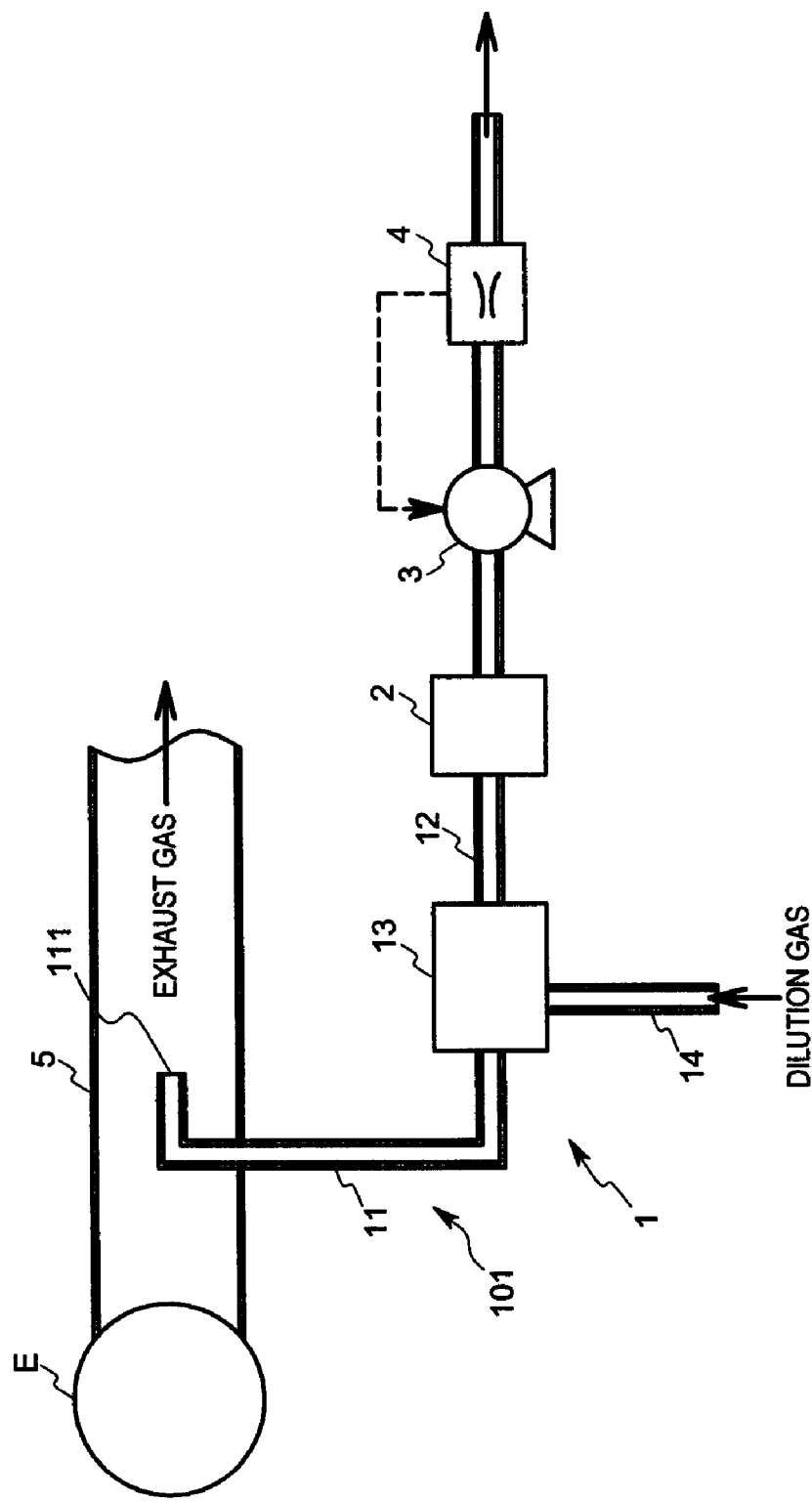
FIG. 1 is a pattern diagram of an analyzer in accordance with an embodiment by the use of an exhaust gas dilution device in accordance with this invention.

An analysis system in accordance with this embodiment comprises, as shown in FIG. 1, an exhaust gas dilution device 1 that introduces and dilutes exhaust gas G from an engine E loaded on, for example, an automobile, a filter 2 that catches particulate matters (PM) contained in the exhaust gas G dilution by the exhaust gas dilution device 1, a vacuum pump 3 that is arranged on a downstream of the filter 2 and a flowmeter 4 such as, for example, a venturimeter, that is arranged on a downstream of the vacuum pump 3.

Figure 2:
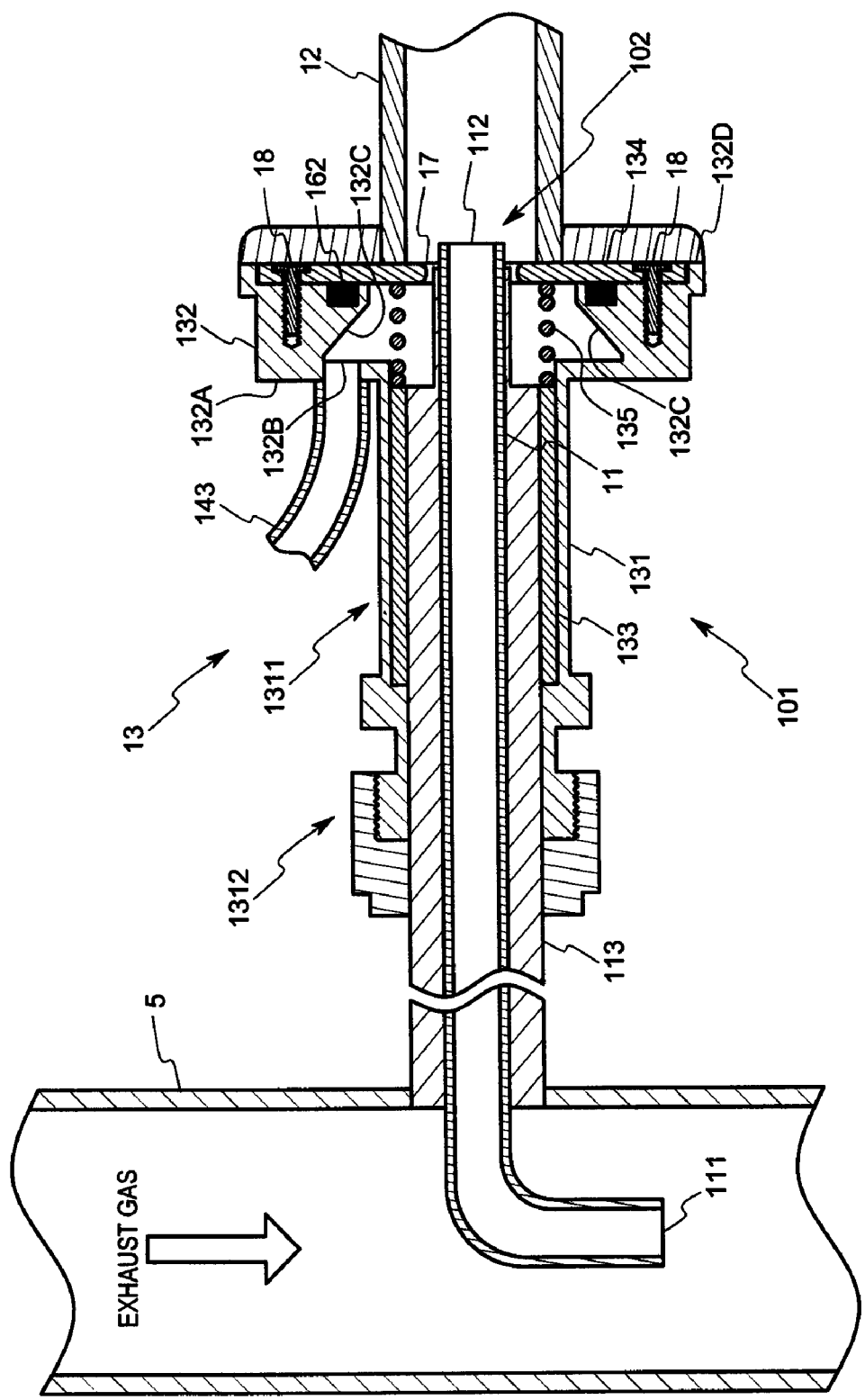
FIG. 2 is a partially enlarged cross-sectional view of the exhaust gas dilution device in accordance with this embodiment.

The exhaust gas dilution device 1 comprises, as shown in FIG. 2, an exhaust gas circulation pipe 101 for circulating the exhaust gas G, a mixing section 102 that is arranged in the exhaust gas circulation pipe 101 and that has an orifice 17, and a dilution gas supply pipe 14 that has an opening at the mixing section 102 and that supplies the dilution gas W to the exhaust gas circulation pipe 101.

The exhaust gas circulation pipe 101 comprises the exhaust gas supply pipe 11 that supplies the exhaust gas G prior to dilution, an exhaust gas transport pipe 12 that circulates the exhaust gas G after dilution and a connecting member 13 that is arranged between the exhaust gas supply pipe 11 and the exhaust gas transport pipe 12.

One side of the exhaust gas supply pipe 11 is inserted into and connected to a side wall of an exhaust pipe 5 for discharging the exhaust gas G of the engine E, and its exhaust gas introduce opening 111 opens toward a direction toward which the exhaust gas G flows. Then the exhaust gas G is supplied to the mixing section 102 at the other side of the exhaust gas supply pipe 11. An exhaust gas supply opening 112 that supplies the exhaust gas G to the mixing section 102 is arranged on the downstream side of the orifice 17, to be described later. In addition, a surrounding area of the exhaust gas supply pipe 11 is covered with a protection pipe 113 including a heat insulating layer so as to prevent the exhaust gas supply pipe 11 from being cooled by the ambient temperature. An outer diameter of the protection pipe 113 gradually decreases from the exhaust gas supply opening 112 by a predetermined length.

The exhaust gas transport pipe 12 is to circulate the exhaust gas G diluted in the mixing section 102, and the filter 2, the vacuum pump 3 and the flowmeter 4 for catching the particulate matters in the exhaust gas G are arranged on the exhaust gas transport pipe 12.

Figure 3:
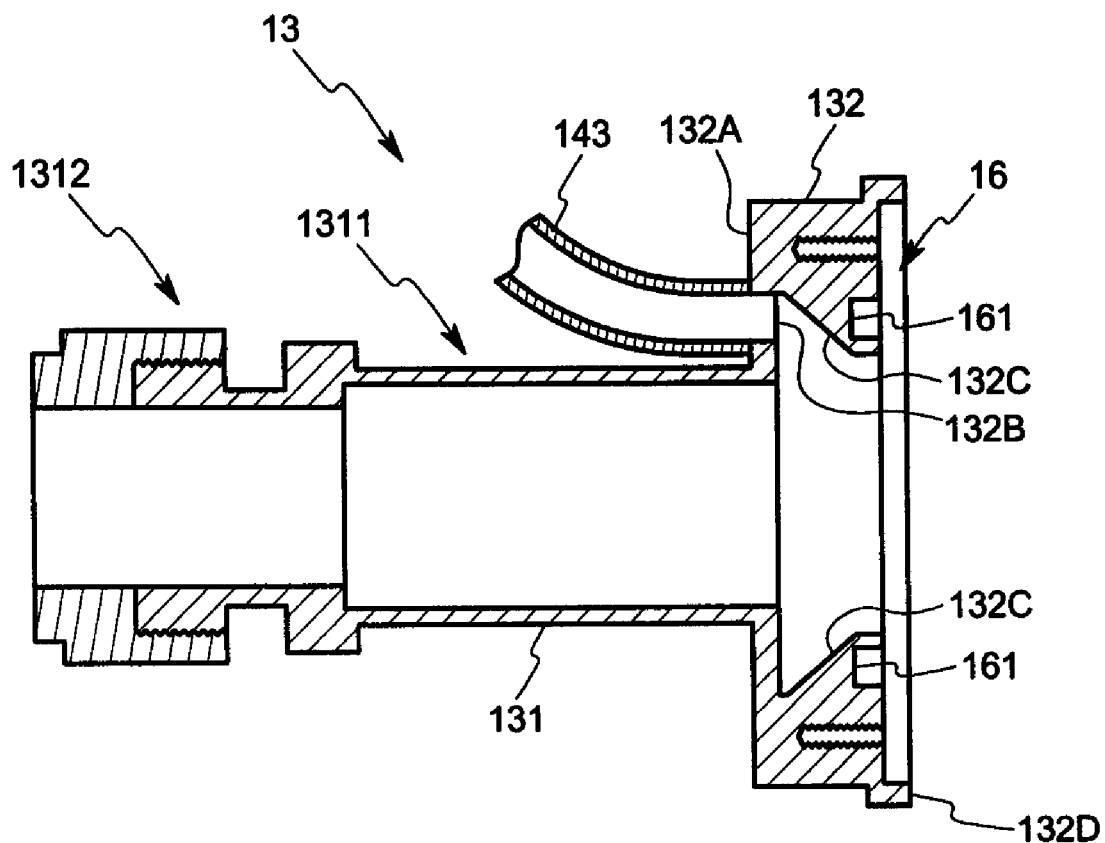
FIG. 3 is a partially enlarged cross-sectional view of a connecting member in accordance with this embodiment.
Figure 4:
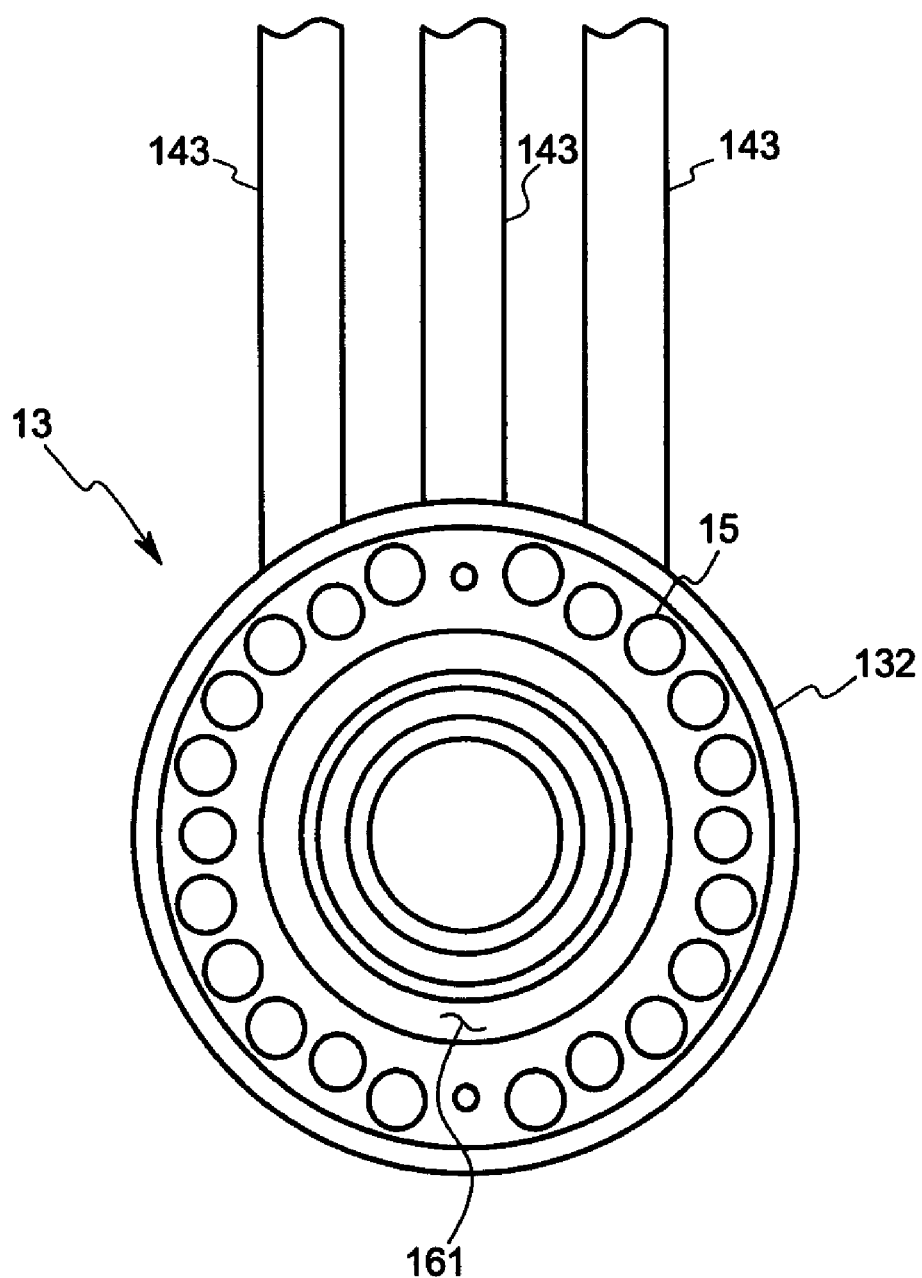
FIG. 4 is a front view of the connecting member in accordance with this embodiment.
Figure 5:
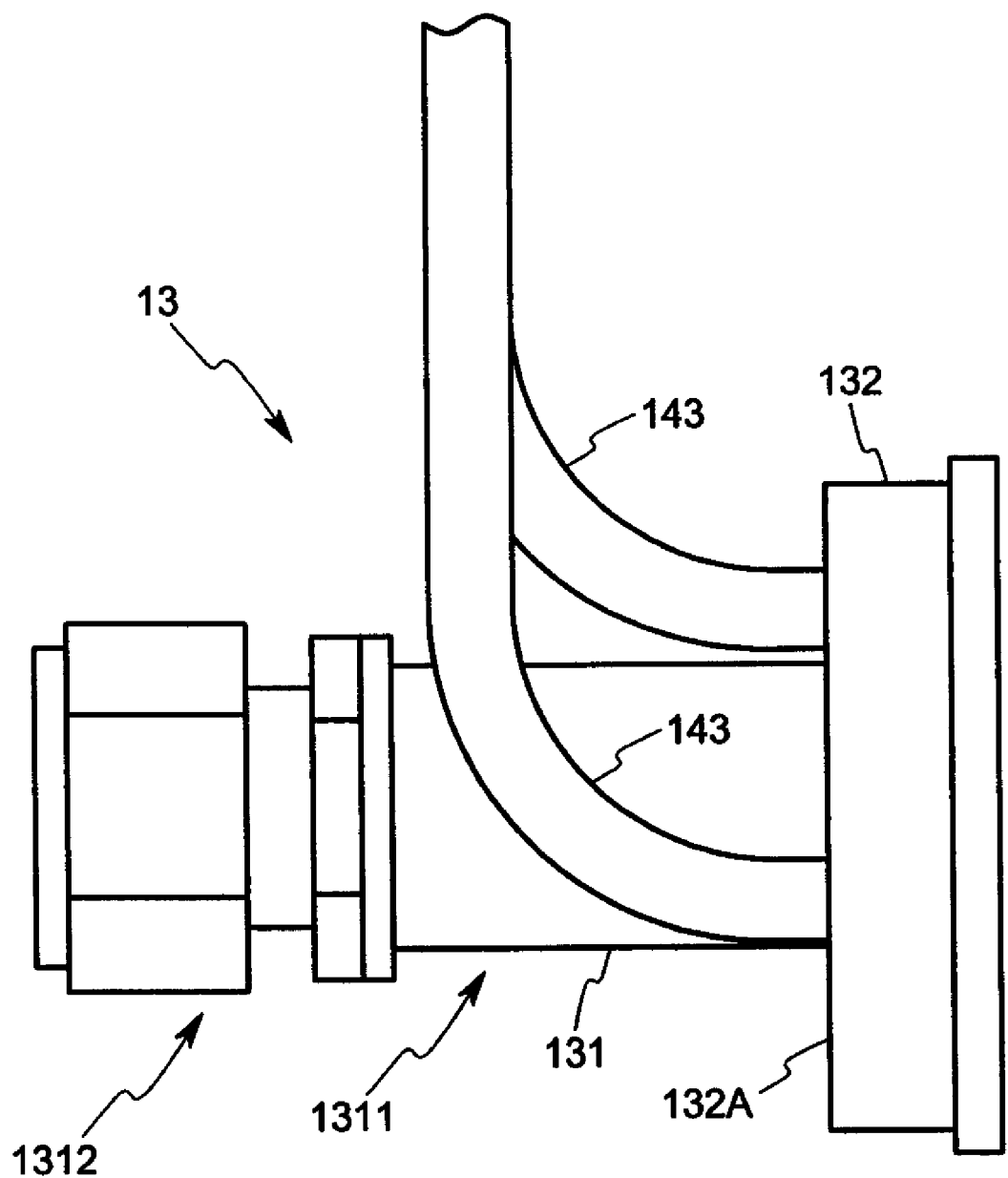
FIG. 5 is a side view of the connecting member in accordance with this embodiment.

The connecting member 13 is, as shown in FIG. 3 through FIG. 5, to connect the exhaust gas supply pipe 11, the exhaust gas transport pipe 12 and the dilution gas supply pipe 14, and comprises a tubular section 131 to be fittingly inserted over an end part, having the exhaust gas supply opening 112, of the exhaust gas supply pipe 11 and a flange section 132 that is continuous to the tubular section 131 and to which the exhaust gas transport pipe 12 and the dilution gas supply pipe 14 are connected.

The tubular section 131 comprises a small diameter section 1312 and a big diameter section 1311 whose inside diameter differs each other, and a tubular heat insulation member 133 is inserted into the big diameter section 1311 for insulating heat from the exhaust gas supply pipe 11 by the use of a circular plate 134 and a coil spring 135, to be described later. Then an inside diameter of the big diameter section 1311 becomes generally equal to that of the small diameter section 1312 in a state wherein the heat insulation member 133 is fittingly inserted into the big diameter section 1311, and an end part of the exhaust gas supply pipe 11 is inserted into the tubular section 131.

The flange section 132 is formed on the downstream side of the tubular section 131 and is of a circular shape. A center part of the flange section 132 forms the mixing section 102, and at a side end face 132A of the tubular section 131, the dilution gas supply pipe 14, to be described later, is arranged spaced apart from the tubular section 131 and generally at right angle to the side end face 132A. In addition, the flange section 132 has a guide face 132C whose diameter gradually decreases toward the downstream at a front of the downstream side of the dilution gas supply opening 132B to make it easier for the dilution gas W that is supplied to the dilution gas supply pipe 14 to be mixed with the exhaust gas G.

Figure 6:
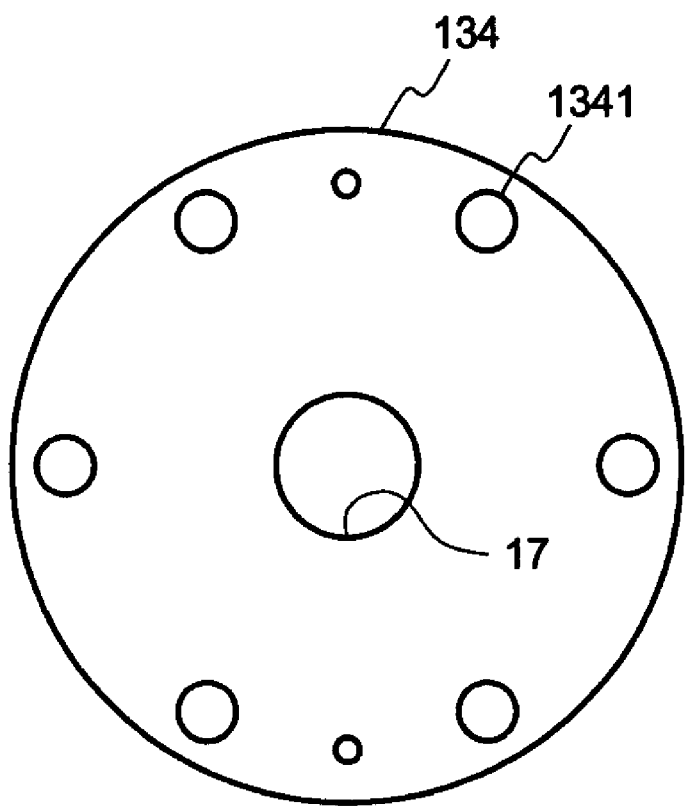
FIG. 6 is a front view of a circular plate in accordance with this embodiment.
Figure 7:
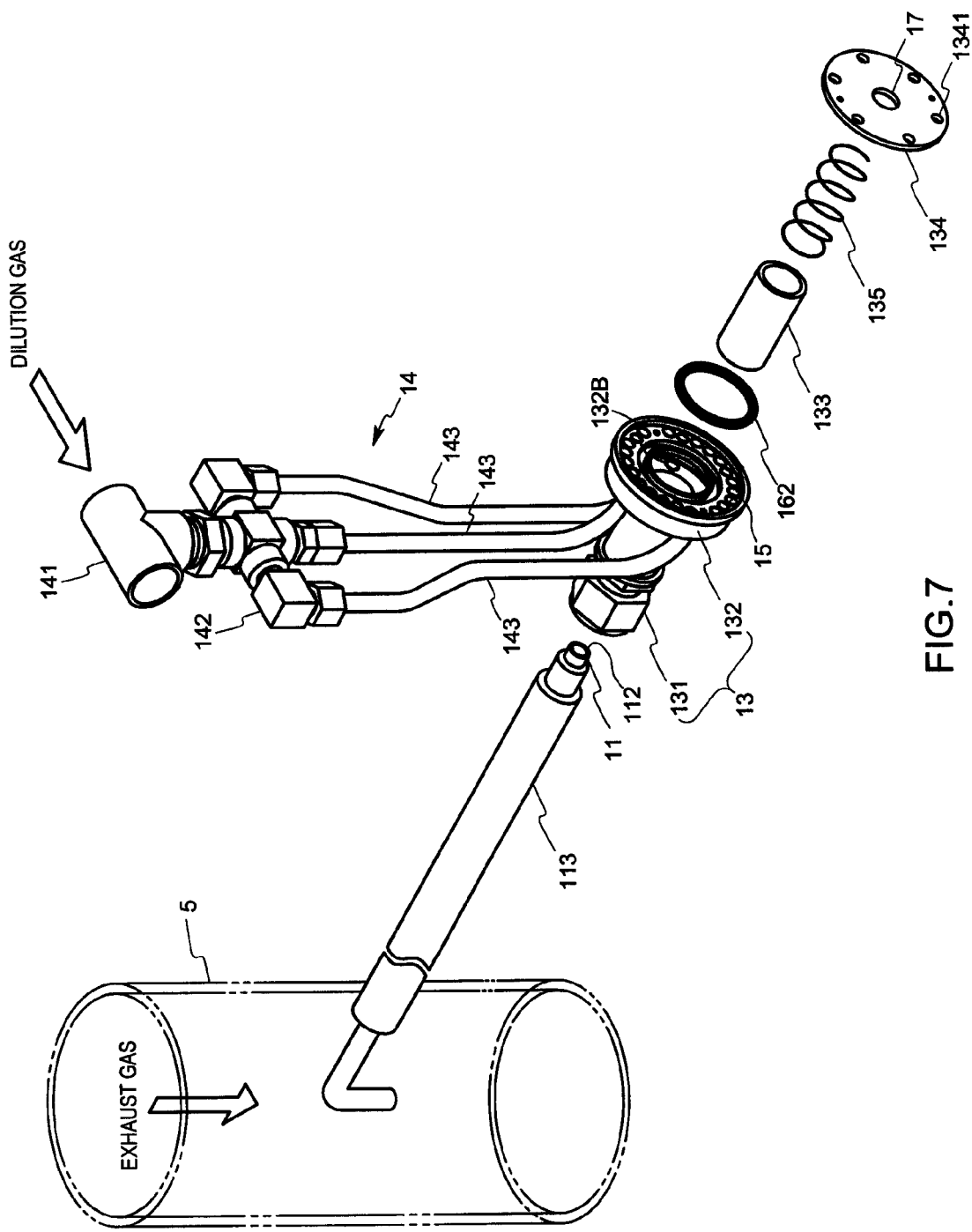
FIG. 7 is an exploded view of the exhaust gas dilution device in accordance with this embodiment.

Furthermore, a heat dissipation device for effectively dissipating the heat from the exhaust gas G, in other words, multiple heat dissipating bores 15 that axially penetrate the flange section 132 are radially arranged at generally even intervals on the flange section 132. In addition, a concave section 16 is arranged on the downstream side end face 132D of the flange section 132 and the circular plate 134 having the orifice 17 shown in FIG. 6 is fittingly inserted into the concave section 16 and fixed by a screw 18. At this time, as shown in FIG. 7, the circular plate 134 is mounted on the flange section 132 with an O-ring 162 fittingly inserted into a ring groove 161 arranged on the concave section 16 and with the heat insulation member 133 and the coil spring 135 placed between the big diameter section 1311 and the circular plate 134 so that the heat insulation member 133 is fittingly inserted into the big diameter section 1311 of the tubular body 131. Then the orifice 17 is formed perpendicular to a direction toward the exhaust gas G circulates. Through bores 1341 are arranged at even intervals on the circular plate 134 so as to coincide with some of the multiple heat dissipating bores 15 arranged on the flange section 132.

Figure 8:
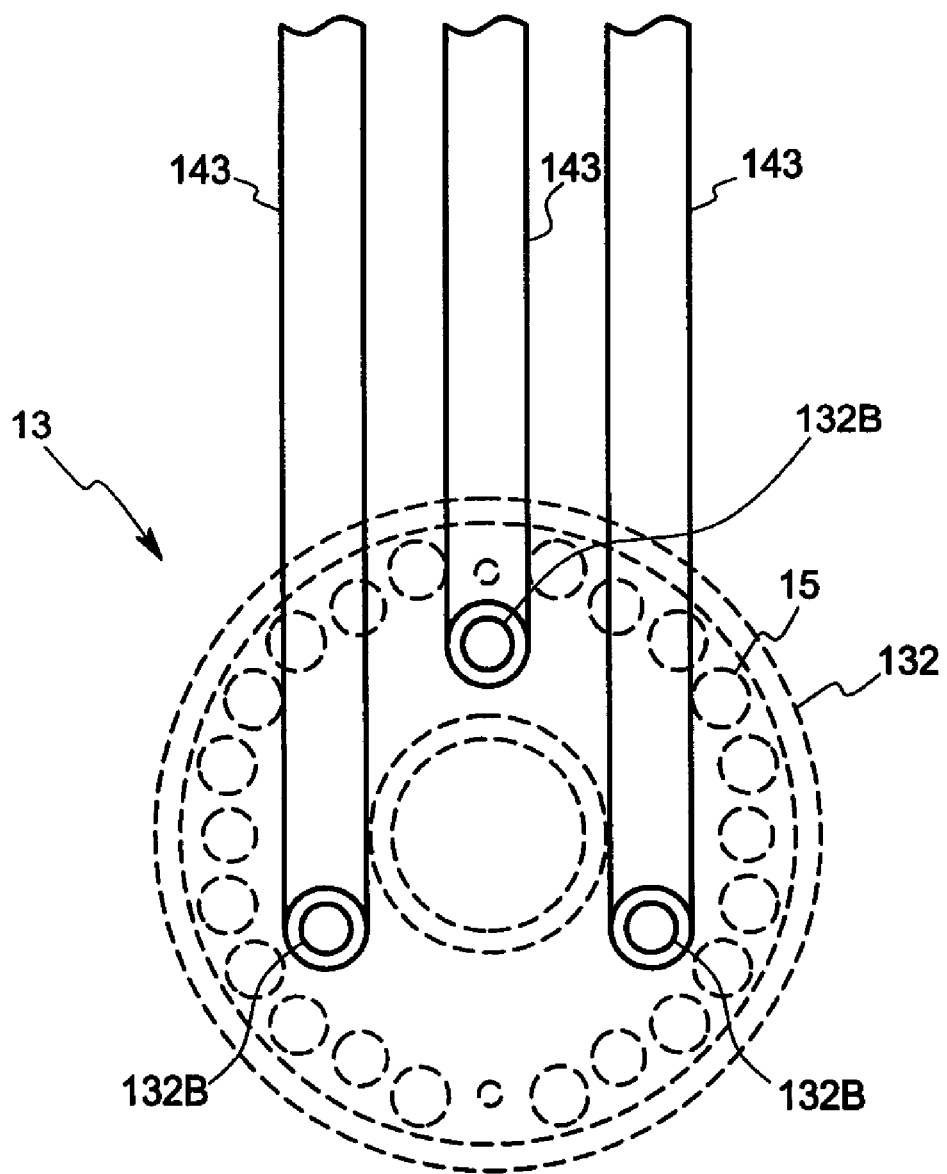
FIG. 8 is a view showing mainly an arrangement of dilution gas supply openings in accordance with this embodiment.
Figure 9:
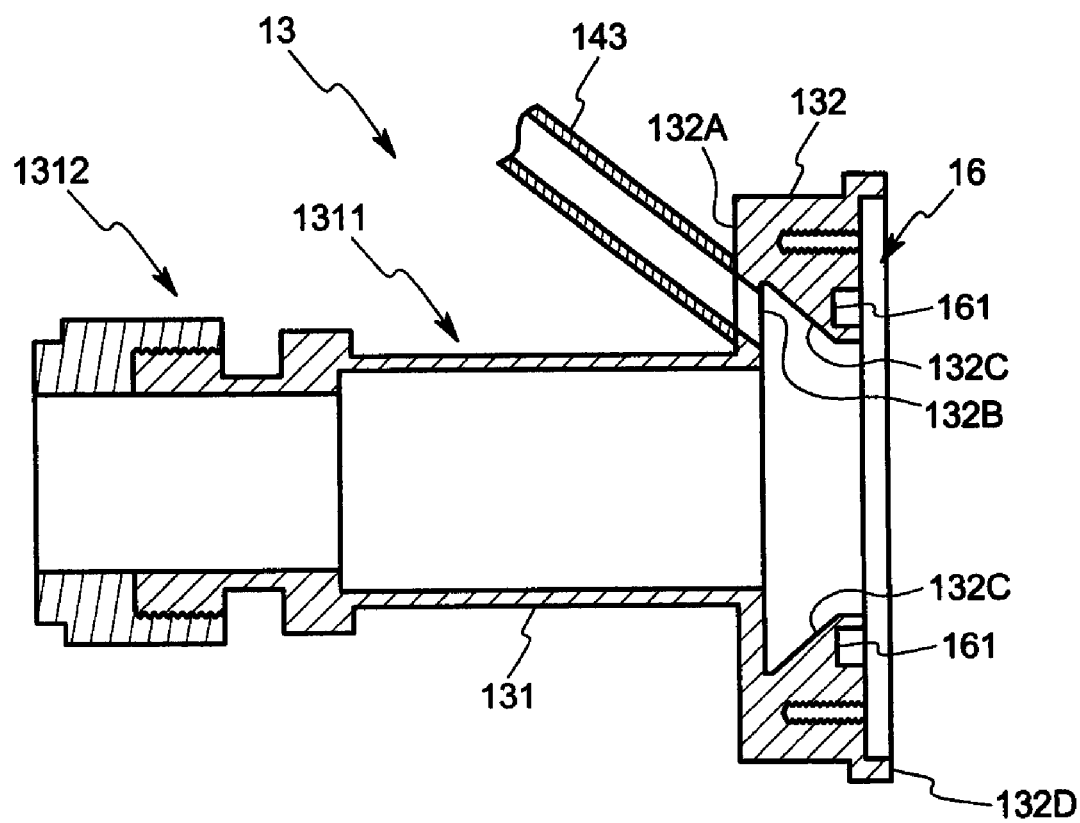
FIG. 9 is a partially enlarged cross-sectional view of a connecting member in accordance with other embodiment.

The dilution gas supply pipe 14 comprises a main pipe 141, trifurcated pipes 142 connected to the main pipe 141 and dilution gas introduce pipes 143 each of which is connected to each of the trifurcated pipes 142 respectively. The dilution gas supply pipe 14 directly introduces the dilution gas W into the mixing section 102. Then as shown in FIG. 8, openings of the mixing section 102 of the dilution gas supply pipe 14, in other words, dilution gas supply openings 132B, of the dilution gas introduce pipe 143, locating at the flange section 132 are arranged at a surrounding area of the exhaust gas circulation pipe 101 at even intervals.

In accordance with the analysis system having this arrangement, since the dilution gas supply pipe 14 and the exhaust gas circulation pipe 101 are arranged spaced apart spatially, it is possible to prevent rise in the temperature of the dilution gas W due to an increased temperature of the exhaust gas circulation pipe 101 prior to mixing the exhaust gas G and the dilution gas W. As a result, the temperature of the exhaust gas G after dilution can be preferably controlled, thereby obtaining accurate measurement results.

In addition, since three dilution gas introduce pipes 143 are arranged and the dilution gas introduce openings 132B of the dilution gas supply pipe 14 are arranged at even intervals to surround the exhaust gas circulation pipe 101, it is possible to dilute the exhaust gas G evenly.

Furthermore, since the heat dissipating bores 15, as being the heat dissipating device, are arranged on the connecting member 13, it is possible to preferably dissipate the heat from the exhaust gas G. As a result, influences on the dilution gas W from the temperature of the exhaust gas G can be further reduced.

The present claimed invention is not limited to the above-mentioned embodiment.

For example, three dilution gas introduce pipes are arranged in the above-mentioned embodiment, however, it is not limited to this and two or four dilution gas introduce pipes may be arranged. At this time, it is preferable to arrange the dilution gas supply openings for each of the dilution gas supply pipes at even intervals.

In addition, the dilution gas supply pipe is connected at generally right angle to the end face of the flange section in the above-mentioned embodiment, however, it is not limited to this and the dilution gas supply pipe may be arranged spaced apart from the exhaust gas supply pipe spatially and the dilution gas supply pipe, more specifically, the dilution gas introduce pipe may be connected to the exhaust gas supply pipe in a tilted state to a direction to which the exhaust gas circulates. With this arrangement, a flow of the dilution gas and the exhaust gas after dilution becomes smooth, thereby preventing the particulate matters from attaching to an inner face of the exhaust gas transport pipe.

Figure 10:
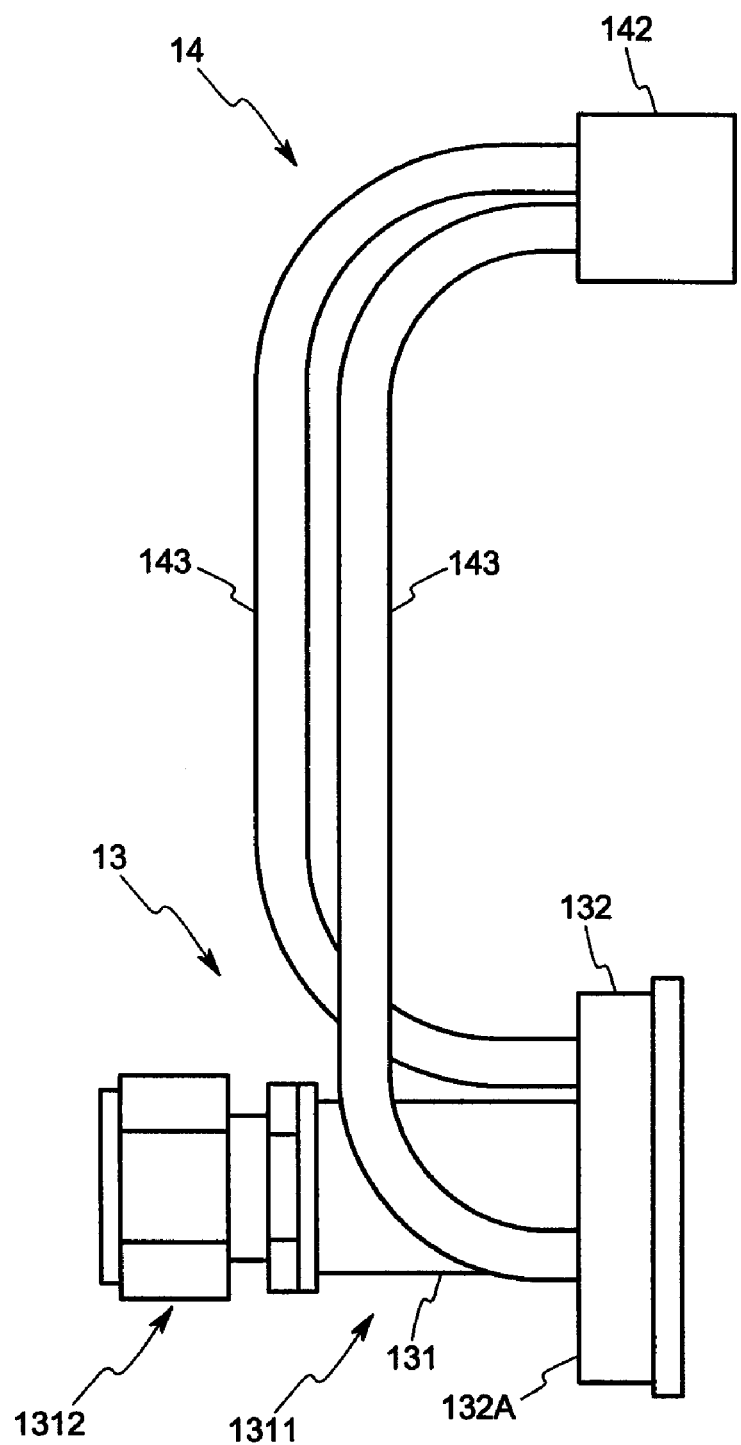
FIG. 10 is a side view of a dilution gas introduce pipe and a connecting member in accordance with an embodiment wherein each length of the dilution gas supply pipes is made to be generally equal.
Figure 11:
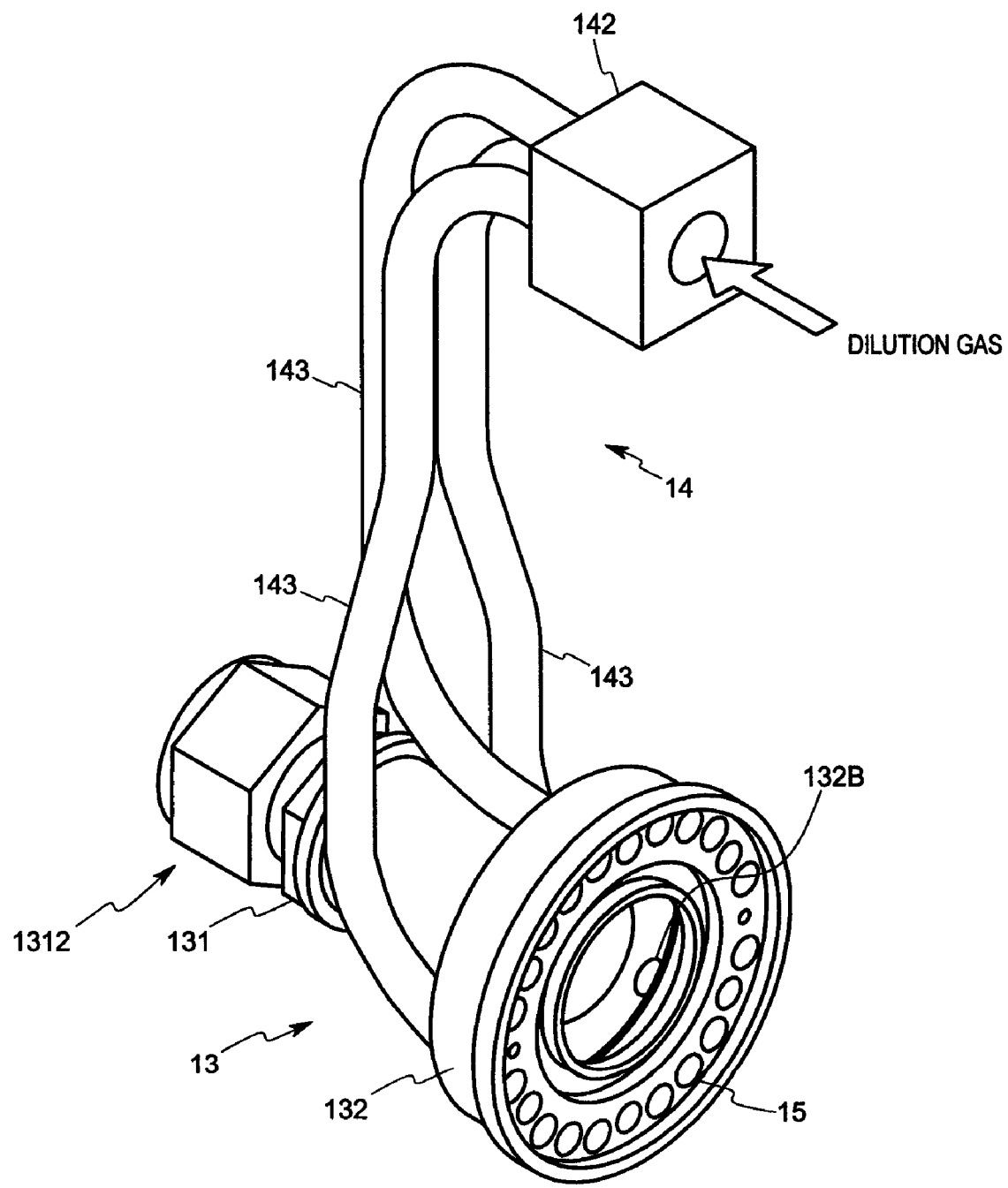
FIG. 11 is a perspective view of the dilution gas introduce pipe and the connecting member in accordance with the embodiment wherein each length of the dilution gas supply pipes is made to be equal.

Furthermore, in order to further equalize the temperature of the exhaust gas after dilution, as shown in FIG. 10 and FIG. 11, each length of the dilution gas supply pipes, in other words, each length of the dilution gas introduce pipes may be made the same.

Figure 12:
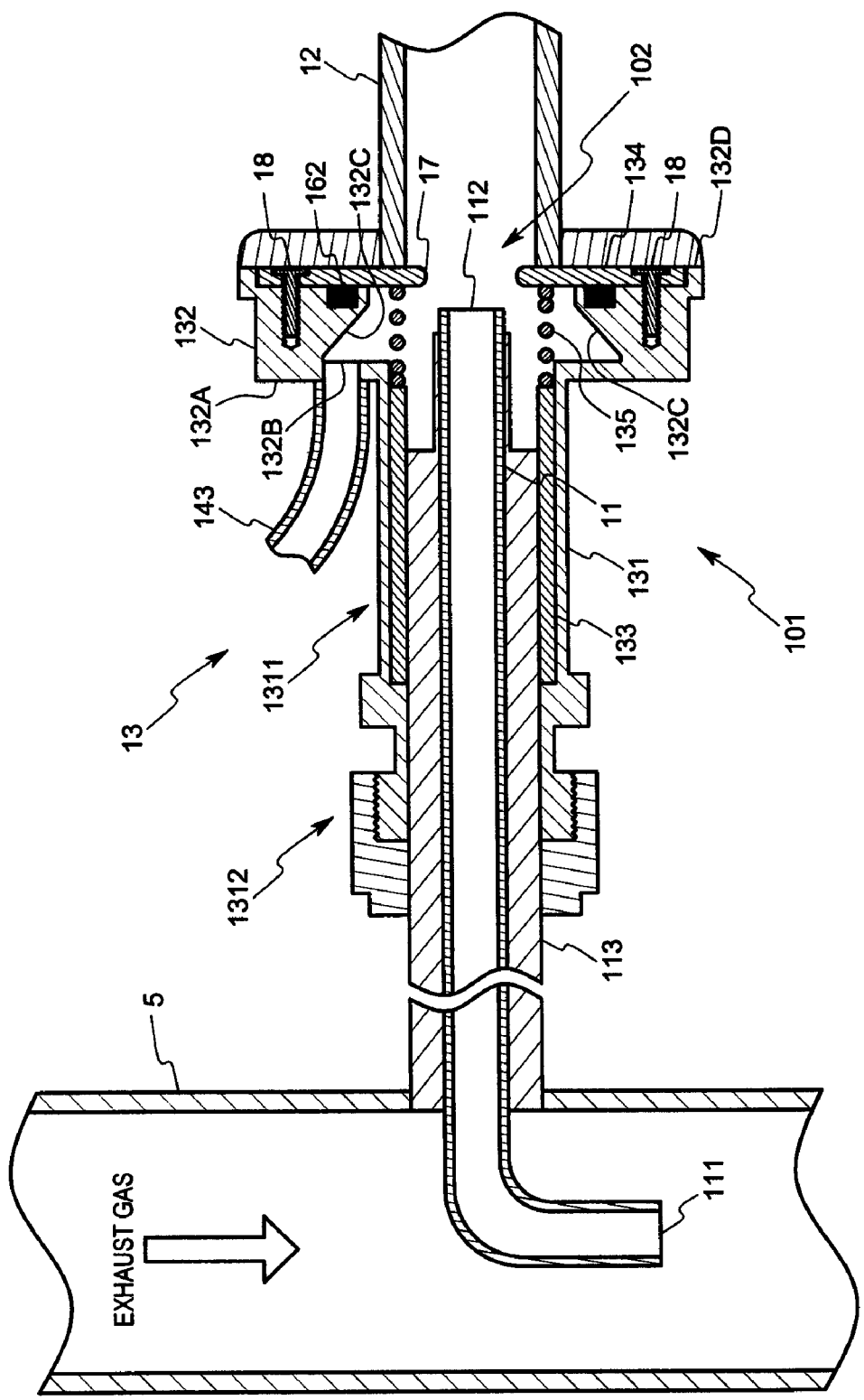
FIG. 12 is a partially enlarged cross-sectional view of an exhaust gas dilution device in accordance with further different embodiment.

In addition, the exhaust gas supply opening is arranged on the downstream side of the orifice in the above-mentioned embodiment, however, it may be arranged on an upstream side of the orifice as shown in FIG. 12.

Furthermore, a part or all of the each embodiment or the modified embodiment may be appropriately combined. The present claimed invention is not limited to each of the above-mentioned embodiments, and may be variously modified without departing from the spirit of the invention.

POSSIBLE APPLICATIONS IN INDUSTRY

As mentioned, in accordance with the analysis system of this arrangement, since the dilution gas supply pipe and the exhaust gas circulation pipe are arranged spaced apart spatially, it is possible to prevent rise in the temperature of the dilution gas due to the increased temperature of the exhaust gas circulation pipe prior to mixing the exhaust gas and the dilution gas. As a result, the temperature of the exhaust gas after dilution can be preferably controlled, thereby obtaining accurate measurement results.

The invention claimed is:

1. An exhaust gas dilution device that dilutes exhaust gas for analyzing a substance contained in the exhaust gas, comprising
    an exhaust gas circulation pipe that circulates the exhaust gas,
    a mixing section that is arranged in a midstream of the exhaust gas circulation pipe and that has an orifice, and
    a dilution gas supply pipe that has an opening near the orifice at the mixing section and that supplies dilution gas to the exhaust gas circulation pipe, wherein
    the dilution gas supply pipe is arranged with spaced apart from the exhaust gas circulation pipe until it reaches the opening near the orifice wherein the exhaust gas circulation pipe comprises an exhaust gas supply pipe that supplies the exhaust gas prior to dilution, an exhaust gas transport pipe that circulates the exhaust gas after dilution and a connecting member that is arranged between the exhaust gas supply pipe and the exhaust gas transport pipe to connect the exhaust gas supply pipe, the exhaust gas transport pipe and the dilution gas supply pipe, and the mixing section is formed in the connecting member.

2. The exhaust gas dilution device, described in claim 1, and comprising two or more dilution gas supply pipes.

3. The exhaust gas dilution device, described in claim 2, wherein the openings at the mixing section of the dilution gas supply pipes are arranged at a surrounding area of the exhaust gas circulation pipe at even intervals.

4. The exhaust gas dilution device, described in claim 2, wherein each of the dilution gas supply pipes has the same length.

5. The exhaust gas dilution device, described in claim 1, and comprising a guide face to guide the dilution gas to be supplied from the dilution gas supply pipe toward a direction toward which the exhaust gas flows.

6. The exhaust gas dilution device, described in claim 1, wherein the exhaust gas circulation pipe comprises the exhaust gas supply pipe to supply the exhaust gas prior to dilution and an exhaust gas transport pipe to circulate the exhaust gas after dilution, and
    an exhaust gas supply opening for supplying the exhaust gas to the mixing section is arranged on the downstream side of the orifice.

7. The exhaust gas dilution device, described in claim 1, wherein a heat dissipation mechanism is arranged at a surrounding area of the mixing section.

8. The exhaust gas dilution device, described in claim 1, wherein
    the connecting member comprises a tubular section to be fittingly inserted over an end part, having the exhaust gas supply opening, of the exhaust gas supply pipe and a flange section that is continuous to the tubular section and to which the exhaust gas transport pipe and the dilution gas supply pipe are connected.

9. The exhaust gas dilution device, described in claim 8, wherein
    the tubular section comprises a small diameter section and a big diameter section whose inside diameter differs each other, and a tubular heat insulation member is inserted into the big diameter section for insulating heat from the exhaust gas supply pipe and
    the inside diameter of the big diameter section becomes generally equal to that of the small diameter section in a state wherein the heat insulation member is fittingly inserted into the big diameter section, and an end part of the exhaust gas supply pipe is inserted into the tubular section.

10. The exhaust gas dilution device, described in claim 8, wherein the flange section is formed on the downstream side of the tubular section and is of a circular shape wherein a center part of the flange section forms the mixing section and the dilution gas supply pipe is arranged at a side end face of the tubular section.

* * * * *

UNITED STATES PATENT AND TRADEMARK OFFICE
CERTIFICATE OF CORRECTION

PATENT NO. : 7,717,002 B2
APPLICATION NO. : 11/915525
DATED : May 18, 2010
INVENTOR(S) : Yasushi Takahashi It is certified that error appears in the above-identified patent and that said Letters Patent is hereby corrected as shown below:

Column 6, Line 4 of Claim 9:

After "diameter differs" insert -- from --.

Signed and Sealed this

Tenth Day of August, 2010

David J. Kappos
*Director of the United States Patent and Trademark Office*